(12) United States Patent
Saevecke et al.

(10) Patent No.: US 11,957,555 B2
(45) Date of Patent: *Apr. 16, 2024

(54) ABSORBENT ARTICLE OR WIPE COMPRISING A NONWOVEN MATERIAL WITH BICOMPONENT FIBERS COMPRISING ANTIMONY-FREE POLYETHYLENE TEREPHTHALATE

(71) Applicant: The Procter & Gamble Company, Cincinnati, OH (US)

(72) Inventors: Dirk Saevecke, Schwalbach am Taunus (DE); Otto Virtanen, Schwalbach am Taunus (DE)

(73) Assignee: The Procter & Gamble Company, Cincinnati, OH (US)

(*) Notice: Subject to any disclaimer, the term of this patent is extended or adjusted under 35 U.S.C. 154(b) by 908 days.

This patent is subject to a terminal disclaimer.

(21) Appl. No.: 16/132,516

(22) Filed: Sep. 17, 2018

(65) Prior Publication Data
US 2019/0105208 A1 Apr. 11, 2019

(30) Foreign Application Priority Data
Oct. 6, 2017 (EP) .................................. 17195228

(51) Int. Cl.
*A61F 13/51* (2006.01)
*A61F 13/511* (2006.01)
(Continued)

(52) U.S. Cl.
CPC ........ *A61F 13/51121* (2013.01); *A61F 13/51* (2013.01); *A61F 13/51401* (2013.01);
(Continued)

(58) Field of Classification Search
CPC ............... A61F 13/51; A61F 13/51121; A61F 13/51401; A61F 13/532; A61F 13/533;
(Continued)

(56) References Cited

U.S. PATENT DOCUMENTS 5,053,482 A 10/1991 Tietz
5,171,308 A 12/1992 Gallagher et al.
(Continued)

FOREIGN PATENT DOCUMENTS

CN 101327156 A 12/2008
CN 101381453 A 3/2009
(Continued)

OTHER PUBLICATIONS

U.S. Appl. No. 16/132,513, filed Sep. 17, 2018, Saevecke et al.
(Continued)

*Primary Examiner* — Catharine L Anderson
(74) *Attorney, Agent, or Firm* — Daniel S. Albrecht; Christian M. Best

(57) ABSTRACT

An absorbent article is provided, the absorbent article comprising a nonwoven material. The nonwoven material comprises core/sheath bicomponent fibers wherein the core is formed of PET resin. The present disclosure also provides a wipe comprising a nonwoven material, the nonwoven material comprising core/sheath bicomponent fibers wherein the core is formed of PET resin. The PET has less than 150 ppm of antimony.

20 Claims, 2 Drawing Sheets

(51) Int. Cl.

| | | |
|---|---|---|
| *A61F 13/514* | (2006.01) | |
| *A61F 13/53* | (2006.01) | |
| *A61F 13/532* | (2006.01) | |
| *A61F 13/537* | (2006.01) | |
| *A61K 8/02* | (2006.01) | |
| *A61L 15/26* | (2006.01) | |
| *A61L 15/60* | (2006.01) | |
| *A61Q 19/10* | (2006.01) | |
| *D04H 1/541* | (2012.01) | |
| *D04H 1/55* | (2012.01) | |
| *D04H 3/011* | (2012.01) | |
| *D04H 3/147* | (2012.01) | |
| *D01F 8/14* | (2006.01) | |

(52) U.S. Cl.
CPC ............ *A61F 13/53* (2013.01); *A61F 13/532* (2013.01); *A61F 13/537* (2013.01); *A61K 8/0208* (2013.01); *A61L 15/26* (2013.01); *A61L 15/60* (2013.01); *A61Q 19/10* (2013.01); *D04H 1/5412* (2020.05); *D04H 1/55* (2013.01); *D04H 3/011* (2013.01); *D04H 3/147* (2013.01); *A61F 2013/51028* (2013.01); *A61F 2013/51452* (2013.01); *A61F 2013/530007* (2013.01); *A61F 2013/530489* (2013.01); *A61F 2013/53051* (2013.01); *A61K 2800/30* (2013.01); *D01F 8/14* (2013.01)

(58) Field of Classification Search
CPC ................. A61F 13/536; A61F 13/537; A61F 2013/51023; A61F 2013/51026; A61F 2013/51028; A61F 2013/51452; D04H 1/43828; D04H 1/5412; D04H 3/147
See application file for complete search history.

(56) References Cited

U.S. PATENT DOCUMENTS

| | | | |
|---|---|---|---|
| 5,171,309 A | | 12/1992 | Gallagher et al. |
| 6,034,202 A | * | 3/2000 | Aharoni ............... B01J 31/0212 |
| | | | 502/102 |
| 7,144,974 B2 | | 12/2006 | Honda et al. |
| 7,371,701 B2 | | 5/2008 | Inagaki |
| 8,759,606 B2 | | 6/2014 | Bond et al. |
| 2003/0114333 A1 | | 6/2003 | Somerville-Roberts et al. |
| 2005/0027267 A1 | | 2/2005 | Van Dyke et al. |
| 2006/0004337 A1 | | 1/2006 | Datta |
| 2006/0057373 A1 | * | 3/2006 | Inagaki ............... D01F 6/62 |
| | | | 428/359 |
| 2015/0065973 A1 | * | 3/2015 | Roe ............... A61F 13/42 |
| | | | 604/361 |
| 2015/0112293 A1 | | 4/2015 | Gust et al. |
| 2015/0337496 A1 | * | 11/2015 | Lee ............... D21C 9/163 |
| | | | 442/327 |
| 2016/0074249 A1 | | 3/2016 | Rosati et al. |
| 2017/0259550 A1 | * | 9/2017 | Neton ............... A61F 13/5116 |
| 2017/0260689 A1 | | 9/2017 | Kramkowski et al. |

FOREIGN PATENT DOCUMENTS

| | | |
|---|---|---|
| CN | 102341081 A | 2/2012 |
| CN | 104470482 A | 3/2015 |
| DE | 202015005969 U1 | 11/2015 |
| EP | 1584723 A1 | 10/2005 |
| EP | 3098295 A1 | 11/2016 |
| EP | 3216433 A1 | 9/2017 |
| WO | 9118036 A1 | 11/1991 |
| WO | 0012792 A1 | 3/2000 |
| WO | 03044155 A1 | 5/2003 |
| WO | WO 2014/146587 A1 | 9/2014 |

OTHER PUBLICATIONS

U.S. Appl. No. 16/132,523, filed Sep. 17, 2018, Saevecke et al.
Search Report and Written Opinion for PCT/US2018/053682 dated Nov. 19, 2018.
All Office Actions for U.S. Appl. No. 16/132,513.
All Office Actions for U.S. Appl. No. 16/132,523.
Extended European Search Report and Search Opinion; Application No. 17195228.6; dated Feb. 26, 2018, 7 pages.
Extended EP Search Report and Written Opinion for 17176188.5 dated Nov. 8, 2017, 7 Pages.

* cited by examiner

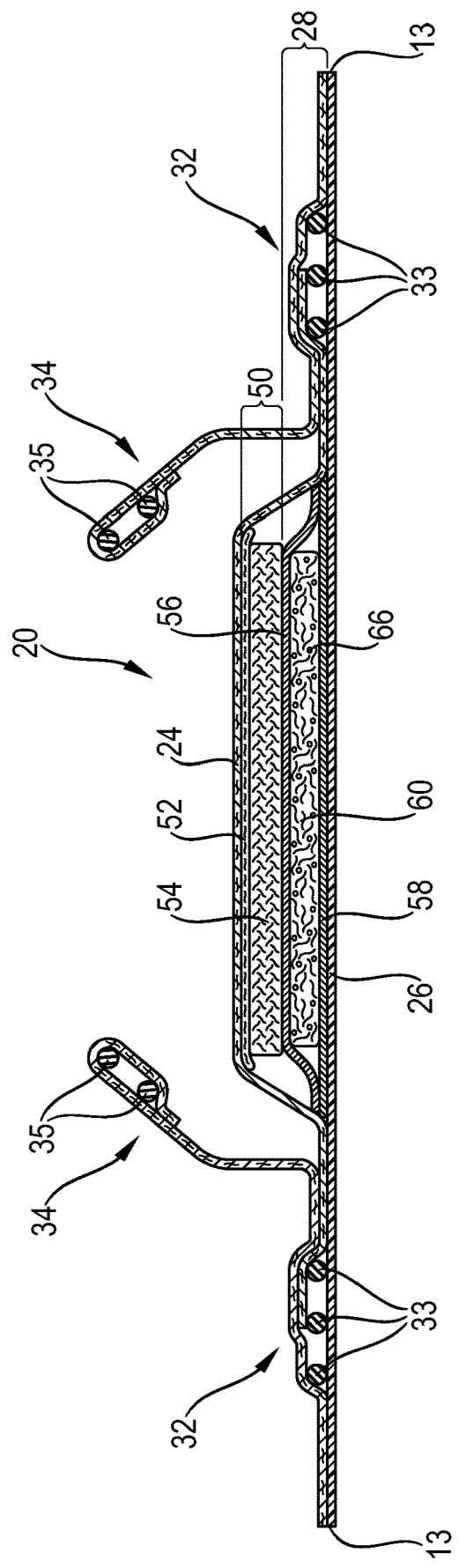

ABSORBENT ARTICLE OR WIPE COMPRISING A NONWOVEN MATERIAL WITH BICOMPONENT FIBERS COMPRISING ANTIMONY-FREE POLYETHYLENE TEREPHTHALATE

CROSS REFERENCE TO RELATED APPLICATION

This application claims priority, under 35 U.S.C. § 119, to European Patent Application Serial No. 17195228.6, filed on Oct. 6, 2017, the entire disclosure of which is hereby incorporated by reference.

FIELD

The present disclosure provides an absorbent article for personal hygiene such as a diaper or pant (for babies, toddlers or adults), a training pant, or a feminine hygiene sanitary napkin. The absorbent article comprises a nonwoven material. The nonwoven material comprises core/sheath bicomponent fibers wherein the core is formed of PET resin. The PET has less than 150 ppm of antimony. The present disclosure also provides a wipe comprising a nonwoven material, the nonwoven material comprising core/sheath bicomponent fibers wherein the core is formed of PET resin. The PET has less than 150 ppm of antimony.

BACKGROUND

Polyethylene terephthalate (PET) is a well known and widely used material. The majority of the world's production of PET is for synthetic fibers (in excess of 60%), with bottle production accounting for about 30% of global demand. In the context of textile applications, PET is typically referred to by its common name, polyester.

PET is also often used in absorbent articles: Many absorbent articles, such as diapers, pants and feminine hygiene articles, comprise one or more nonwoven webs which comprise polyethylene terephthalate (PET).

PET is industrially produced by esterification or transesterification of terephthalic acid or dimethyl terephthalate and ethylene glycol to produce bis(2-hydroxyethyl) terephthalate which is then subjected to polycondensation at high temperatures in vacuo in the presence of a catalyst. As a conventional polyester polymerization catalyst used in polycondensation of polyester, antimony trioxide.

As a consequence of the use of an antimony compound as catalyst, traces of the antimony can be found in the PET resin and thus, also in the nonwoven web comprised by the absorbent article. Trace amounts of antimony in PET are typically in the range of 200 to 300 ppm.

Antimony is reported to have a negative impact on the environment and carcinogenic potential. Though the typical amounts of antimony in the PET resin are extremely low and not considered to be critical, increased attention on this chemical compound has been raised by consumers.

PET resin made by a process, which uses a catalyst other than antimony compounds, is known in the art, for example in CA02420958 assigned to Toyo Boseki Kabushiki Kaisha, JP; EP1316585B1 assigned to Invista Technologies, CH; EP1491572A1 assigned to Toray Industries, Inc, JP; EP1153953B1 and EP1327648A1, both assigned to Toyo Boseki Kabushiki Kaisha, JP; For example, a known approach to PET resin processing technology is to implement a titanium-containing polycondensation catalyst as a replacement for the conventional antimony-containing polycondensation catalyst. However, such titanium-containing polycondensation catalyst typically gives a yellowish color to the resultant PET resin, rendering the PET polyester fiber manufactured therefrom less commercially desired due to its yellowish look.

To reduce the yellowish look, it has been suggested to add a phosphorus stabilizer during the PET resin process in order to reduce the yellowish look of the PET resin caused by the titanium-containing polycondensation catalyst. For instance, U.S. Patent Application Publication US 2006/0014920A1 assigned to Teijin Fibers discloses a mixture-based catalyst mixed by tetrabutyltitanate (TBT), product of reaction of TBT and trimellitic anhydride, and triethyl phosphonoacetate (TEPA).

Though antimony free PET has been disclosed in the prior art, to date it has not found wide use in the industry, as most commercially available antimony free PET resins still have a yellowish color.

In absorbent articles and wipes, the use of antimony free PET has not been suggested so far. One of the reasons is supposed to be related to the yellowish color, which consumers perceive as low quality. This appears to be specifically critical as absorbent articles and wipes get into direct contact with the delicate skin, especially the skin of babies and toddlers.

SUMMARY

Absorbent article comprising a topsheet forming a wearer-facing surface of the absorbent article, a backsheet forming a garment-facing surface of the absorbent article and an absorbent core interposed between the topsheet and the backsheet, wherein the absorbent article comprises a nonwoven material.

The nonwoven material comprises at least 20%, by weight of the nonwoven material, of core/sheath bicomponent fibers. The core component of the core/sheath bicomponent fiber is formed of polyethylene terephthalate (PET) and the sheath component is formed of a thermoplastic polymer other than PET.

The PET comprises less than 150 ppm of antimony. The core component having an a* value unequal zero; and having a b* value unequal zero.

The nonwoven material may be a nonwoven web. Alternatively, the nonwoven material may be fibers which are comprised by a component of the absorbent article, such as the absorbent core, without being in the form of a web.

The a* value of the core component may be less than −0.6, or less than −0.7, or from −2.0 to −0.6, or from −1.5 to −0.7, or from −1.5 to −0.8.

The b* value of the core component may be higher than 1.5, or higher than 1.8, or from 1.5 to 5.0, or from 1.5 to 3.5.

The nonwoven material may comprise at least 30%, or at least 50%, or at least 70% or at least 80%, or 100%, by weight of the nonwoven material, of the core/sheath bicomponent fibers having a core component formed of PET with less than 150 ppm of antimony.

The PET comprised by the core component may have less than 100 ppm, less than 75 ppm, less than 50 ppm, less than 10 ppm of antimony, or may be completely antimony-free (i.e. 0 ppm of antimony).

The antimony content of the PET may be measured by microwave digestion of the PET resin under pressure ($HNO_3$ and HCL) and subsequent determination of antimony by Inductively coupled plasma mass spectrometry (ICP-MS). Determination of antimony content in PET can, for example, be done by GALAB Laboratories GmbH, Hamburg; Germany. Measuring the antimony content in the PET in accordance with ISO 105 E04, which uses less harsh digestion methods and Artificial Acid Sweat Solution, may not lead to determination of the complete antimony content in the PET, so this method should not be followed for the present disclosure.

The delta E* between the core component of the bicomponent fiber and the core component covered by the sheath component may be at least 1, or may be at least 2, or may be at least 3, or may be at least 4, or may be at least 5. The delta E* is measured according to the test method set out below.

The sheath component may a content of titanium dioxide of from 0.1% to 2.0%, or from 0.1% to 1.5%, by weight of the sheath component.

The sheath component may form at least 25%, or at least 30%, or at least 40%, or at least 60%, or at least 65%, by weight, of the bicomponent fiber. The sheath component may form not more than 95%, or not more than 90%, or not more than 85%, or not more than 80% by weight, of the bicomponent fiber.

The sheath component may constitute more than 30%, or more than 40%, or more than 50%, or more than 60%, or more than 70%, or even more than 80% of the diameter of the bicomponent fiber such the sheath component is able to cover the core component in a suitable manner.

The core/sheath bicomponent fiber may have a concentric core component.

The sheath component may have an opacity of at least 10%, or at least 15%, or at least 20%, or at least 30%, or at least 40%. The sheath component may have an opacity of not more than 80%, or not more than 70%.

The absorbent core of the absorbent article may comprise a combination of cellulose fibers and superabsorbent polymer particles, and the absorbent core may comprise areas which are free of cellulose fibers and superabsorbent polymer particles. The areas being free of cellulose fibers and superabsorbent polymer particles may be elongated areas having a length of from 20% and 80%, or from 20% to 70%, or from 30% to 60%, by total longitudinal dimension of the absorbent article.

The present disclosure is also directed to a wipe, such as a wipe comprising lotion and intended for cleaning the human body. The wipe comprises or consists of a nonwoven material, the nonwoven material comprising at least 20%, by weight of the nonwoven material, of core/sheath bicomponent fibers. The core component of the core/sheath bicomponent fiber is formed of polyethylene terephthalate (PET) and the sheath component is formed of a thermoplastic polymer. The PET comprises less than 150 ppm of antimony. The core component having an a* value unequal zero; and having a b* value unequal zero.

BRIEF DESCRIPTION OF THE DRAWINGS

While the specification concludes with claims particularly pointing out and distinctly claiming the present disclosure, it is believed that the same will be better understood from the following description read in conjunction with the accompanying drawings in which:

FIG. 2 is a transversal cross-section of the diaper of FIG. 1.

DETAILED DESCRIPTION

Definition of Terms

Figure 1:
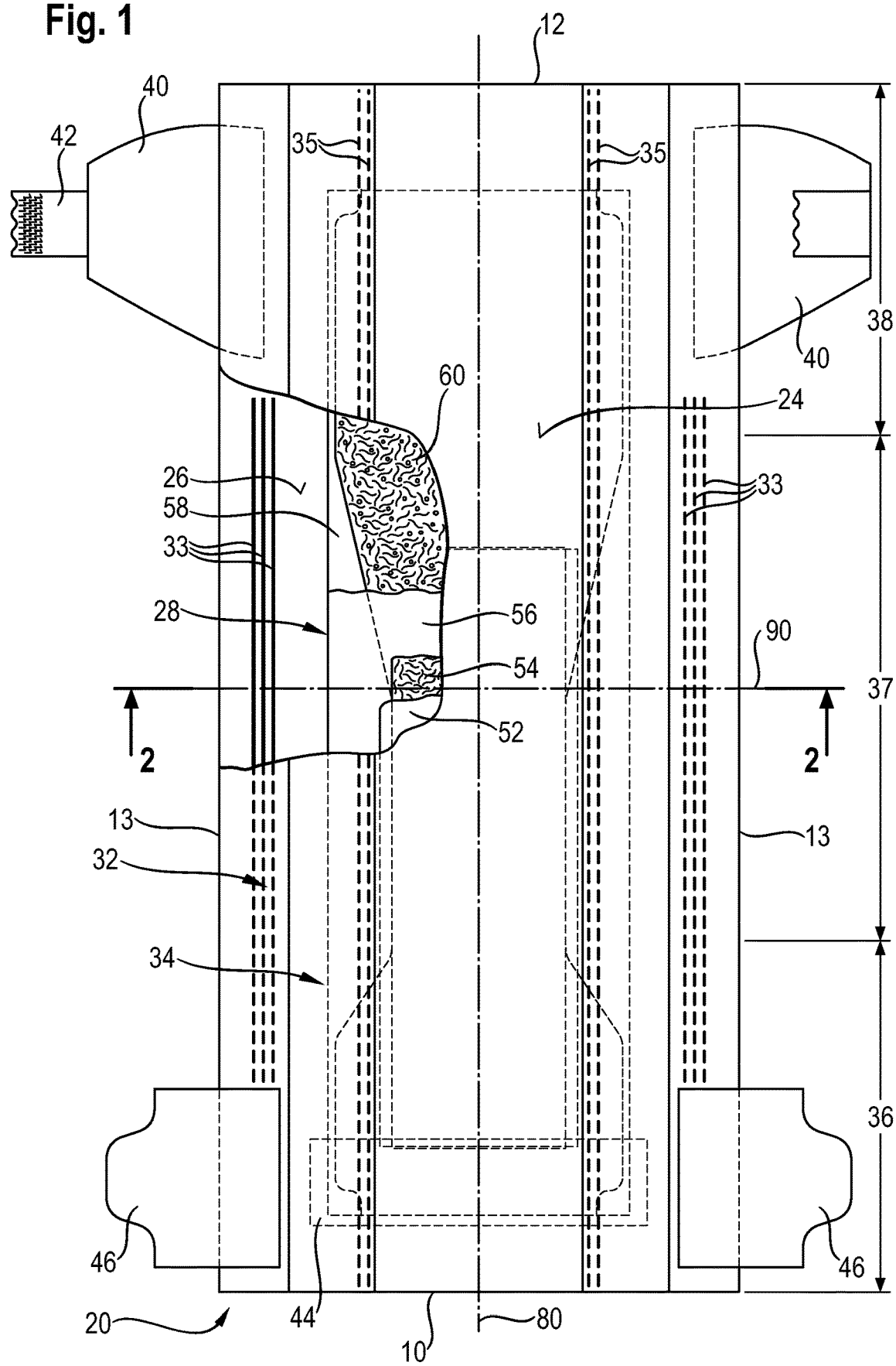
FIG. 1 is an example absorbent article in the form of a diaper.

As used herein, "absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants (for babies or for adults), absorbent inserts (which are intended to be inserted into an outer cover to form a diaper or pant), feminine care absorbent articles such as sanitary napkins or pantiliners, and the like. As used herein, the term "exudates" includes, but is not limited to, urine, blood, vaginal discharges, sweat and fecal matter. Absorbent articles of the present disclosure may be disposable absorbent articles, such as disposable diapers and disposable pants.

The term "absorbent core" as used herein refers to a component, which is placed or is intended to be placed within an absorbent article and which comprises an absorbent material enclosed in a core wrap. The term "absorbent core" does not include an acquisition or distribution layer or any other component of an absorbent article which is not either an integral part of the core wrap or placed within the core wrap. The absorbent core is typically the component of an absorbent article which comprises all, or at least the majority of, superabsorbent polymer and has the highest absorbent capacity of all the components of the absorbent article.

"Bicomponent" refers to fibers having a cross-section comprising two discrete polymer components, two discrete blends of polymer components, or one discrete polymer component and one discrete blend of polymer components. "Bicomponent fiber" is encompassed within the term "multicomponent fiber." A bicomponent fiber may have an overall cross section divided into two subsections of the differing components of any shape or arrangement, including, for example, concentric core/sheath subsections, eccentric core/sheath subsections, side-by-side subsections, radial subsections, etc. The bicomponent fibers used in the present disclosure are core/sheath bicomponent fibers, i.e. they comprise a core component surrounded by a sheath component. The core component may be arranged eccentric or concentric within the sheath component.

"Color", as used herein, includes any color in the CIELAB color space including primary color, secondary color, tertiary color, the combination thereof, as well as black and white.

CIE L*a*b* ("CIELAB") is the most commonly used color space specified by the International Commission on Illumination (French Commission internationale de l'éclairage, hence its CIE initialism). It describes all the colors visible to the human eye and was created to serve as a device independent model to be used as a reference.

The three coordinates of CIELAB represent the lightness of the color (L*=0 yields black and L*=100 indicates white), its position between red/magenta and green (a*, negative values indicate green while positive values indicate magenta) and its position between yellow and blue (b*, negative values indicate blue and positive values indicate yellow). The asterisk (*) after L, a and b are part of the full name, since they represent L*, a* and b*, to distinguish them from Hunter's L, a, and b.

As used herein, "diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

As used herein, "disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a diaper, a pant, sanitary napkin, sanitary pad or wipe for personal hygiene use, the disposable absorbent article is most often intended to be disposed after single use.

"Monocomponent" refers to fiber formed of a single polymer component or single blend of polymer components, as distinguished from bicomponent or multicomponent fiber.

"Multicomponent" refers to fiber having a cross-section comprising two or more discrete polymer components, two or more discrete blends of polymer components, or at least one discrete polymer component and at least one discrete blend of polymer components. "Multicomponent fiber" includes, but is not limited to, "bicomponent fiber." A multicomponent fiber may have an overall cross section divided into subsections of the differing components of any shape or arrangement, including, for example, coaxial subsections, concentric core-and-sheath subsections, eccentric core-and-sheath subsections, side-by-side subsections, islands-in the sea subsection, segmented pie subsections, etc.

A "nonwoven material" is a compilation of nonwoven fibers. The nonwoven material may or may not be in web form, i.e. it may or may not be in the form of a consolidated web which has integrity and is self-sustaining. The fibers which may be comprised by the nonwoven material are the same as those set out below for a nonwoven web.

A "nonwoven web" is a nonwoven material which is a manufactured web of directionally or randomly oriented fibers, consolidated and bonded together, e.g. by one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers (which are subsequently molten) or may be provided in liquid, such as a styrene butadiene binder. A liquid binder is provided to the fibers (e.g. by spraying, printing or foam application) and is subsequently cured to solidify. The term "nonwoven" does not include fabrics which are woven, knitted, or stitch-bonded with yarns or filaments. The fibers may be of natural or man-made origin and may be staple or continuous filaments. Nonwoven fabrics can be formed by many processes such as meltblowing, spunlaid, solvent spinning, electrospinning, and carding. As used herein, "spunlaid" refers to fibers made by spunbond technology without having undergone further processing, such as bonding. The basis weight of nonwoven fabrics is usually expressed in grams per square meter ($g/m^2$). For the present disclosure, a multilayered nonwoven web may be consolidated and bonded by hydroentanglement and/or needle punching, in addition to being consolidated and bonded by bonds obtained by heat and/or compression (including ultrasonic bonding), e.g. in order to impart improved loft to the nonwoven web. Carded webs are formed of short, so-called staple fibers. They are typically formed into a layer of fibers and subsequently consolidated into a nonwoven web, for example by applying a binder to the fibers (as described above), by autogenously bonding the fibers together with heat and/or by intertwining the fibers by known processes such as hydroentangling or needle-punching. The carded fibers may also be bonded together, e.g. by one or more patterns of bonds and bond impressions created through localized compression and/or application of heat or ultrasonic energy, or a combination thereof.

As used herein, a "pantiliner" and a "sanitary napkin" generally have two end regions and a middle region (i.e. a crotch region). The pantiliner and the sanitary napkin have a body-facing surface and a garment facing surface. The size and shape of the absorbent structure positioned between the topsheet and the backsheet can be altered to meet absorbent capacity requirements, and to provide comfort to the wearer. The garment facing surface of the pantiliner and of the sanitary napkin can have thereon pressure sensitive adhesive for affixing to a wearer's undergarments. Typically, such adhesive is covered with a release strip which is removed before affixing to the undergarment. Pantiliners can also be provided with lateral extensions known commonly in the art as "flaps" or "wings" intended to extend over and cover the panty elastics in the crotch region of the user's undergarment. However, wings are normally not used with pantiliners but are more often used in sanitary napkins. Sanitary napkins and pantiliners of the present disclosure comprise barrier leg cuffs.

The term "wipe", as used herein, refers to an article comprising a sheet of fibrous material. Wipes are also known to as "cleaning sheet". Wipes, either dry or wet, are intended to be used for removal of a substance from a surface or object which is animate or inanimate, or alternatively, application of a material to a surface or object which is animate or inanimate. For instance, wipes may be used for cleaning hard surfaces, such as floors. Wipes may also be used for human or animal cleansing or wiping such as anal cleansing, perineal cleansing, genital cleansing, and face and hand cleansing. Wipes may also be used for application of substances to the body, including but not limited to application of make-up, skin conditioners, ointments, and medications. They may also be used for cleaning or grooming of pets. Additionally, they may be used for general cleansing of surfaces and objects, such as household kitchen and bathroom surfaces, eyeglasses, exercise and athletic equipment, automotive surfaces, and the like. In the present disclosure, a wipe may be a cleaning sheet for human cleaning. The wipe may be a wipe and comprise a lotion. The wipe may be a wet wipe.

In more details, FIG. 1 is a plan view of an example diaper 20, in a flat-out state, with portions of the diaper being cut-away to more clearly show the construction of the diaper 20. As said, this diaper 20 is shown for illustration purpose only as the structure of the present disclosure may be comprised in a wide variety of diapers or other absorbent articles, such as pants.

As shown in FIG. 1, the absorbent article, here a diaper, can comprise a liquid pervious topsheet 24, a liquid impervious backsheet 26, an absorbent core 28 which is positioned between the topsheet 24 and the backsheet 26. The absorbent core 28 can absorb and contain liquid received by the absorbent article and may comprise absorbent materials 60, such as superabsorbent polymers 66 and/or cellulose fibers, as well as other absorbent and non-absorbent materials commonly used in absorbent articles (e.g. thermoplastic adhesives immobilizing the superabsorbent polymer particles). The absorbent article of the present disclosure, such as the diaper 20 illustrated in FIG. 1, may optionally also include an acquisition system with an upper 52 and lower 54 acquisition layer.

The diaper also comprises barrier leg cuffs 34 and may further comprise elasticized leg cuffs 32. Moreover, the absorbent article may comprise a fastening system, such as an adhesive fastening system or a hook and loop fastening member, which can comprise tape tabs 42, such as adhesive tape tabs or tape tabs comprising hook elements, cooperating with a landing zone 44 (e.g. a nonwoven web providing loops in a hook and loop fastening system).

The diaper or pant, such as the diaper 20 shown in FIG. 1 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper (the same applies to for the transversal centerline and longitudinal line of other absorbent articles of the present disclosure). The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20. The crotch region, the first and the second waist region each constitutes ⅓ of the absorbent article along the longitudinal centerline.

Further, the diaper may comprise other elements, such as a back waist feature, which may be non-elastic or elastic, and a front waist feature, which may be non-elastic or elastic, a lotion applied onto the wearer-facing surface of the topsheet, back ears 40, and/or front ears 46.

The front and/or back ears 40, 46 may be separate components attached to the diaper or may instead be continuous with portions of the topsheet and/or backsheet—and/or even portions of the absorbent core—such that these portions form all or a part of the front and/or back ears 40, 46. Also combinations of the aforementioned are possible, such that the front and/or back ears 40, 46 are formed by portions of the topsheet and/or backsheet while additional materials are attached to form the overall front and/or back ears 40, 46. The front and/or back ears may be elastic or non-elastic.

The topsheet 24, the backsheet 26, and the absorbent core 28 may be assembled in a variety of well known configurations, in particular by gluing, heat embossing, ultrasonic bonding or combinations thereof. Example diaper configurations are described generally in U.S. Pat. No. 3,860,003; 5,221,274; 5,554,145; 5,569,234; 5,580,411; and 6,004,306.

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

The backsheet may comprise a backsheet outer cover material (sometimes referred to as a backsheet nonwoven) 40. The backsheet outer cover material may comprise one or more nonwoven materials joined to a backsheet film 28 and that covers the backsheet 28. The outer cover material 40 may form the garment-facing surface of the backsheet so that film is not present on the garment-facing surface. The backsheet outer cover material 40 may comprise a bond pattern, apertures, and/or three-dimensional features.

As set out in the background section above, PET resin which has been produced with a catalyst other than antimony generally leads to a resin with a yellowish color. Therefore, while the inventors found it desirable to use PET resin which has been produced with a catalyst other than antimony, they realized that the yellow color will not be accepted by consumers.

When considering the known processes described in the background section, which attempt to avoid the yellowing of the PET resin with other catalyst systems, it has been found that these processes typically apply substances such as inks, or phosphorous compounds. The presence of such substances in the PET resin has been identified as not being desirable, as they may give rise to health and environment related concerns as well, so replacing antimony with another substance that might be considered as problematic, has been found to be non-preferred.

The inventors have found that a nonwoven material comprising PET can be used in absorbent articles or wipes despite the yellowish color of the PET resin having less than 150 ppm of antimony, if the PET resin forms the core component of a core/sheath bicomponent fiber. The sheath component of the bicomponent fiber can facilitate a significant reduction of the visibility of the yellowish color of the core component.

The core/sheath bicomponent fibers may have a concentric core component such that the sheath component has the same thickness everywhere across the diameter of the bicomponent fibers. That way, the yellowish color of the core component, formed by the PET resin having an antimony content of less than 150 ppm, is uniformly covered across the fiber diameter.

The sheath component may form at least 25%, or at least 30%, or at least 40%, or at least 60%, or at least 65%, by weight, of the bicomponent fiber. The sheath component may form not more than 95%, or not more than 90%, or not more than 85%, or not more than 80% by weight, of the bicomponent fiber.

The sheath component may constitute more than 30%, or more than 40%, or more than 50%, or more than 60%, or more than 70%, or even more than 80% of the diameter of the bicomponent fiber such the sheath component is able to cover the core component in a suitable manner.

The sheath component of the bicomponent fiber may comprise a white pigment, such as titanium dioxide. For example, the sheath component may comprise from 0.5% to 5.0%, or from 0.8% to 3.0%, or from 0.8% to 2.5%, or from 1.0% to 2.0%, by weight of the sheath component, of titanium dioxide to increase the whiteness and opacity of the sheath component. $TiO_2$ also provides brightness and relatively high refractive index. However, because $TiO_2$ is a relatively hard, abrasive material, inclusion of $TiO_2$ in amounts greater than 5.0% by weight may have deleterious effects, including wear and/or clogging of spinnerets; interruption and weakening of the structure of the fibers and/or calendar bonds there between; undesirably increasing the surface friction properties of the fibers (resulting in a less smooth tactile feel); and unacceptably rapid wear of downstream processing equipment components. While 5.0% by weight $TiO_2$ may be an upper limit, it may be more desirable to have no more than 4.0% or no more than 3.0% or no more than 2.0% $TiO_2$ by weight of the sheath component.

The nonwoven material comprising bicomponent fibers, with a core component formed from PET with less than 150 ppm antimony, may be provided between the topsheet and the absorbent core. It may be in direct contact with the topsheet of the absorbent article.

For example, the absorbent article may comprise an acquisition system provided between the absorbent core and the topsheet and the nonwoven material, comprising bicomponent fibers, with a core component formed from PET with less than 150 ppm antimony, may be comprised by the acquisition system, such as forming an upper layer of an acquisition system which is in direct contact with the topsheet.

Alternatively or in addition to being provided between the topsheet and the absorbent core, the nonwoven material, comprising bicomponent fibers, with a core component formed from PET with less than 150 ppm antimony, may also be provided between the backsheet and the absorbent core of the absorbent article.

Still alternatively or in addition to being provided between the topsheet and the absorbent core, and/or between the backsheet and the absorbent core, the nonwoven material, comprising bicomponent fibers, with a core component formed from PET with less than 150 ppm antimony, may be comprised by or may form the topsheet and/or the backsheet. In such circumstances, the nonwoven material, comprising bicomponent fibers, with a core component formed from PET with less than 150 ppm antimony, may form that portion of the wearer-facing surface and/or the garment-facing surface of the absorbent article, which is formed by the topsheet and/or backsheet, respectively.

Suitable nonwoven webs comprising the PET with less than 150 ppm of antimony—comprising the core/sheath bicomponent fibers wherein the core component is formed from PET resin with less than 150 ppm of antimony—

Suitable nonwoven material—comprising the core/sheath bicomponent fibers wherein the core component is formed from PET resin with less than 150 ppm of antimony—comprise nonwoven webs comprising spunlaid layers, meltblown layers, layers of nanofibers or combinations of such layers. Generally, the diameter of spunlaid fibers is larger compared to the diameter of meltblown fibers, which in turn have a somewhat larger diameter than nanofibers. Spunlaid fibers typically have a diameter of 8 μm to 40 μm; meltblown fibers have a diameter of 0.5 μm to <8 μm, while nanofibers generally have a diameter of 0.01 μm to 1.5 μm. Nanofibers can be made by different processes, including advanced meltblown as disclosed in U.S. Pat. No. 7,922,943B2, melt film fibrillation as disclosed in U.S. Pat. No. 7,931,457B2 or electrospinning as disclosed in U.S. Pat. No. 6,616,435B2. The spunlaid fibers may also have non-circular cross-sections, in which case the major and minor axes of the cross-sectional shape have lengths in the range from 8 μm to 40 μm. However, for the bicomponent fibers it may be desired that the fibers have a circular cross-section such that the sheath component may form a more uniform "cover" for the core component.

The nonwoven material, such as a nonwoven web, may also be made of carded fibers (so-called staple fibers) or the nonwoven material may be a multilayer nonwoven web comprising one or more layers of carded fibers and one or more layers of spunlaid, meltblown and/or nano fibers. Examples include, but are not limited to SMS multilayer nonwoven webs, comprising a spunlaid, a melt-blown and a further layer. Another suitable multilayer nonwoven webs of the present disclosure comprise webs having a SMMS-structure (two outer spunlaid layers and two inner meltblown layers) or a SMMMS-structure (two outer spunlaid layers with three inner meltblown layers). Other suitable multilayered nonwoven webs have a SNS structure, comprising a spunlaid, a nanofiber and a further spunlaid layer, or SMNS webs, comprising a spunlaid, a meltblown, a nanofiber and a further spunlaid layer.

Nonwoven webs having spunlaid fibers forming the outer surfaces of the nonwoven web tend to have better resistance to fuzz, i.e. the fibers exposed to the surface of the nonwoven web are not as easily abraded and twitched out of the nonwoven web as fine fibers with smaller diameters (such as meltblown fibers or nanofibers). This may be especially beneficial when the nonwoven web forms at least a part of the garment-facing surface of a disposable absorbent article, such as a diaper, where the garment-facing surface is rubbed against clothes or other items (such as carpets) when the article is worn.

On the other hand, nonwoven webs, wherein the outer surface of the web is formed of a meltblown fibers or nanofibers may be able to provide a more uniform appearance on the outer surface at a given basis weight of the fiber layer as the fibers have a considerably smaller diameter.

The PET having less than 150 ppm of antimony may also be free of dyes, pigments, hues and optical brighteners, as such compounds include substances which have recently also gained increased attention with regard to potential adverse effects for the human health and the environment. The same applies to phosphorous compounds which are comprised by some antimony-free PET resins previously suggested, where a phosphorus stabilizer is used in the PET resin manufacturing process to reduce the yellowish color. Also, some antimony-free PET resins described in the art may comprise trimellitic anhydride, and triethyl phosphonoacetate (TEPA) and the presence of these compounds is not desirable for use of the PET resin in absorbent articles and wipes.

The nonwoven material (as a whole) comprising PET with less than 150 ppm antimony may be free of dyes, pigments, hues and optical brighteners, and/or may be free of phosphorous substances, and/or may be free of trimellitic anhydride, and triethyl phosphonoacetate.

The nonwoven material comprising bicomponent fibers, with a core component formed from PET with less than 150 ppm antimony, comprises at least 10%, by weight of the nonwoven material, of such PET. The nonwoven material may comprise at least 30%, or at least 50%, or at least 70%, or 100%, by weight of the nonwoven material, of bicomponent fibers, with a core component formed from PET with less than 150 ppm antimony. If the nonwoven material comprises less than 100% bicomponent fibers, with a core component formed from PET with less than 150 ppm antimony, the nonwoven material may further comprise fibers formed of a thermoplastic material other than PET, such as polyolefin, polyamide, or specifically polypropylene (PP), polyethylene (PE), poly-lactic acid (PLA), Nylon 6-6 as well as combinations thereof (such as blends and copolymers). Such other fibers may comprise monocomponent fibers and/or multicomponent fibers, such as bicomponent fibers.

The nonwoven material may not comprise any PET having more than 150 ppm, or more than 100 ppm, or more than 75 ppm, or more than 50 ppm, or more than 10 ppm of antimony, or may not comprise any PET which is not completely antimony-free (i.e. zero ppm).

The absorbent article or the wipe may not comprise any PET having more than 150 ppm, or more than 100 ppm, or more than 75 ppm, or more than 50 ppm, or more than 10 ppm of antimony, or may not comprise any PET which is not completely antimony-free (i.e. zero ppm).

The PET having less than 150 ppm of antimony may be provided as homopolymer of PET, as copolymer (co-PET) or as a combination thereof. A combination thereof may include a mixture of fibers comprising homopolymer of PET and fibers comprising co-PET.

PET consists of polymerized units of the monomer ethylene terephthalate, with repeating $(C_{10}H_8O_4)$ units.

In co-PET, for example, cyclohexane dimethanol (CHDM) can be added to the polymer backbone in place of ethylene glycol. Since this building block is much larger (6 additional carbon atoms) than the ethylene glycol unit it replaces, it does not fit in with the neighboring chains the way an ethylene glycol unit would. This interferes with crystallization and lowers the polymer's melting temperature. In general, such PET is known as PETG or PET-G (Polyethylene terephthalate glycol-modified; Eastman Chemical, SK Chemicals, and Artenius Italia are some PETG manufacturers).

Another common modifier for obtaining co-PET is isophthalic acid, replacing some of the 1,4-(para-) linked terephthalate units. The 1,2-(ortho-) or 1,3-(meta-) linkage produces an angle in the chain, which also disturbs crystallinity.

All of the fibers of the nonwoven material may be formed from thermoplastic material, such as polyolefin, polyamide or specifically polypropylene (PP), polyethylene (PE), poly-lactic acid (PLA), polyethylene terephthalate (PET), Nylon 6-6 as well as combinations thereof (such as blends and copolymers), in addition to comprising the bicomponent fibers wherein the core component comprises PET with less than 150 ppm of antimony. However, the nonwoven material may, in addition to the bicomponent fibers, with a core component formed from PET with less than 150 ppm antimony, also comprise fibers made of non-thermoplastic fibers, such as natural fibers. Such natural fibers include, for example, cotton or cellulose fibers. The natural fibers may be provide as one or more separate layers in the nonwoven material, and/or they be mixed with the other, non-natural, fibers.

Generally, resins including PP may be particularly useful because of polypropylene's relatively low cost, low density and surface friction properties of fibers formed from it (i.e., they have a relatively smooth, slippery tactile feel), as well as their good mechanical properties. Resins including PE may also be desirable because of polyethylene's relative softness/pliability and even more smooth/slippery surface friction properties. Relative each other, PP currently has a lower cost and fibers formed from it have a greater tensile strength, while PE currently has a greater cost and fibers formed from it have a lower tensile strength but greater pliability and a more smooth/slippery feel. Multicomponent fibers from PP and PE are desirable for as they combine the good softness properties of PP and the good mechanical properties of PE.

The thermoplastic polymer suitable for the fibers comprised by the nonwoven webs of the present disclosure may also be thermoplastic starch. As used herein, "thermoplastic starch" or "TPS" means a native starch or a starch derivative that has been rendered destructured and thermoplastic by treatment with one or more plasticizers, with at least one starch plasticizer still remaining. Thermoplastic starch compositions are well known and disclosed in several patents, for example: U.S. Pat. Nos. 5,280,055; 5,314,934; 5,362,777; 5,844,023; 6,214,907; 6,242,102; 6,096,809; 6,218,321; 6,235,815; 6,235,816; and 6,231,970.

The nonwoven web material may have any basis weight. However, relatively higher basis weight, while having relatively greater apparent caliper and loft, also has relatively greater cost.

The basis weight for the nonwoven material comprising bicomponent fibers with a core component formed from PET with less than 150 ppm antimony, may be 200 g/m² or less, or may be from 5 g/m² to 120 g/m², or from 10 g/m² to 100 g/m², or from 15 g/m² to 80 g/m², or from 30 g/m² to 60 g/m².

It may generally be desirable to have nonwoven materials with relatively homogeneous distribution of fibers, i.e. webs wherein the fibers have been laid down homogeneously, especially for nonwoven materials with relatively low basis weight.

If the nonwoven material comprises other fibers or materials (such as, e.g., binder) in addition to the fibers comprising PET with less than 150 ppm of antimony, the fibers comprising PET with less than 150 ppm of antimony may be homogeneously distributed within the nonwoven material.

The nonwoven material, comprising bicomponent fibers with a core component formed from PET with less than 150 ppm antimony, be a carded nonwoven web. The fibers of the carded nonwoven fibrous web(s) are staple fibers. The carded nonwoven web, comprising bicomponent fibers with a core component formed from PET with less than 150 ppm antimony, may comprise a binder, such as a liquid latex binder which has been cured after application onto the fibers to solidify. Alternatively, the carded nonwoven web, comprising bicomponent fibers with a core component formed from PET with less than 150 ppm antimony, may not comprise a liquid binder which has been cured to solidify.

For example, a carded nonwoven web, comprising bicomponent fibers with a core component formed from PET with less than 150 ppm antimony, may comprise at least 50%, or from 60% to 90%, or from 60% to 80% by weight of the carded nonwoven web, of staple fibers and at least 10%, or from 10% to 40%, or from 20% to 40%, by weight of the carded nonwoven web, of a latex binder. Staple fibers are short fibers. They may have a length of from 10 mm to 120 mm, or from 25 mm to 80 mm, or from 25 mm to 60 mm. The staple fibers may be straight or, alternatively, may have two-dimensional or three-dimensional crimp. Crimped staple fibers can improve the resiliency of the nonwoven web, which is generally desirable when the nonwoven web is comprised by an acquisition system of the absorbent article.

In another example, a carded nonwoven web, comprising bicomponent fibers with a core component formed from PET with less than 150 ppm antimony, may comprise staple fibers which have been autogeneously bonded to each other, e.g. by subjecting the carded fibers to a through-air bonding process. Such carded nonwoven webs will typically not comprise a liquid binder (such as a latex binder) which has been cured to solidify after application onto the fibers.

Carding is a mechanical process using staple fibers. To obtain staple fibers, the fibers are first spun, cut to a few centimeters length. The cut fibers are combed into a layer of fiber material by a carding machine, such as a rotating drum or series of drums covered in fine wires or teeth.

In contrast to carded nonwoven webs, spunlaid and meltblown nonwoven webs are typically made in one continuous process. Fibers are spun and then directly dispersed into a web by deflectors or directed with air streams. The fibers of a spunlaid or meltblown nonwoven are considerably longer compared to staple fibers.

The sheath component of the bicomponent fibers, comprising bicomponent fibers with a core component formed from PET with less than 150 ppm antimony, may be made of a polymer which has a melting point below the melting point of the PET that forms the core. If such bicomponent fibers are subjected to through-air bonding or calendar bonding, the temperature of the through air bonding process or the bonding calendar is typically selected such that the polymer of the sheath component is at least partially transferred to a molten state (or partly molten state, or molten to a state where the fiber surface becomes sufficiently tacky) such that the fibers bond together while the core component of the bicomponent fiber remains substantially unaffected.

The shape of the bicomponent fibers, with a core component formed from PET with less than 150 ppm antimony, may be round (i.e. fibers having a circular cross-section). Alternatively, the fibers may have non-round shape, such as multilobal fibers (e.g. trilobal fibers), flat fibers ("ribbon-like" cross-section), rhomboid fibers or triangular fibers. In multilobal fibers, a central section is encircled by a multiplicity of lobes. E.g. in a trilobal fiber, the central section is encircled by three lobes. The nonwoven material, comprising bicomponent fibers with a core component formed from PET with less than 150 ppm antimony, may also comprise a mixture of fibers having different shapes, such as a mixture of round and multilobal fibers. However, for the bicomponent fibers with a core component formed from PET with less than 150 ppm antimony, it is preferred that the fibers have a circular cross-section such that the sheath component may form a more uniform "cover" for the core component.

Wipes

A wipe may be a wet wipe comprising lotion and intended for cleaning the human body. The wipe comprises or consists of a nonwoven material, the nonwoven material comprising at least 20%, by weight of the nonwoven material, of core/sheath bicomponent fibers. The core component of the core/sheath bicomponent fiber is formed of polyethylene terephthalate (PET) and the sheath component is formed of a thermoplastic polymer. The PET comprises less than 150 ppm of antimony. The core component having an $a^*$ value unequal zero; and having a $b^*$ value unequal zero.

The nonwoven material comprised by the wipe, or the nonwoven material of which the wipe consists, may be a nonwoven web.

The $a^*$ value of the core component may be less than −0.6, or less than −0.7, or from −2.0 to −0.6, or from −1.5 to −0.7, or from −1.5 to −0.8.

The $b^*$ value of the core component may be higher than 1.5, or higher than 1.8, or from 1.5 to 5.0, or from 1.5 to 3.5.

The nonwoven material may comprise at least 30%, or at least 50%, or at least 70% or at least 80%, or 100%, by weight of the nonwoven material, of the core/sheath bicomponent fibers having a core component formed of PET with less than 150 ppm of antimony.

The PET comprised by the core component may have less than 100 ppm, or less than 75 ppm, or less than 50 ppm, or less than 10 ppm of antimony, or may be completely free of antimony (i.e. zero ppm of antimony).

The delta $E^*$ between the core component of the bicomponent fiber and the core component covered by the sheath component may be at least 1, or may be at least 2, or may be at least 3, or may be at least 4, or may be at least 5. The sheath component may a content of titanium dioxide of from 0.1% to 2.0%, or from 0.1% to 1.5%, by weight of the sheath component.

The sheath component may form at least 25%, or at least 30%, or at least 40%, or at least 60%, or at least 65%, by weight, of the bicomponent fiber. The sheath component may form not more than 95%, or not more than 90%, or not more than 85%, or not more than 80% by weight, of the bicomponent fiber.

The sheath component may constitute more than 30%, or more than 40%, or more than 50%, or more than 60%, or more than 70%, or even more than 80% of the diameter of the bicomponent fiber such the sheath component is able to cover the core component in a suitable manner.

The core/sheath bicomponent fiber may have a concentric core component.

The sheath component may have an opacity of at least 10%, or at least 15%, or at least 20%, or at least 30%, or at least 40%. The sheath component may have an opacity of not more than 80%, or not more than 70%.

Test Methods

Measurement of $a^*$, $b^*$, $L^*$ and Delta $E^*$ Values

The measurement is based on the CIE $L^*$ $a^*$ $b^*$ color system (CIELAB). $L^*$, $a^*$ and $b^*$ may be measured using a 0.deg. illumination/45.deg. detection, circumferential optical geometry, spectrophotometer with a computer interface such as the HunterLab LabScan® XE running Universal Software (available from Hunter Associates Laboratory Inc., Reston, VA). The HunterLab LabScan® XE is equipped with a Port Down Stand, which enables measurement of the sample from a straight-down angle. Instrument calibration and measurements are to be made using the standard protocol by the vendor. All testing is performed in a room maintained at about 23° C.±2° C. and about 50%±2% relative humidity.

Configure the spectrophotometer for the L*, a*, b* color value scale, D65 illuminant, 10.deg. standard observer, with UV filter set to nominal. Standardize the instrument according to the manufacturer's procedures using the 1.20 inch port size and 1.00 inch area view.

To obtain the specimen, the thermoplastic material forming the core component of the bicomponent fibers, i.e. the PET resin having less than 150 ppm of antimony, is taken from the manufacturing process prior to being incorporated into the bicomponent fibers. The material is heated to above is melting temperature to be sufficiently low viscous to be poured onto a surface in order to form a film of substantially homogeneous basis weight.

100 g of the heated core component material is poured onto a plate (with a flat, even base plate coated with Teflon™) having a size of 100 cm by 100 cm (the height is not critical but may be 20 mm) to form a homogeneous layer. The tablet is left standing at room temperature until the thermoplastic material has solidified into a film layer of 100 g/m$^2$. The film is carefully removed from the tablet and measured for reference L*, a*, b* values.

The same procedure is followed for obtaining film of 100 g/m$^2$ from the thermoplastic material used for the sheath component of the core/sheath bicomponent fiber. The film of sheath component is carefully removed from the tablet and placed on top of the film of core component. The L*, a* and b* values are measured for the specimen with the film of sheath component covering the film of core component. The sheath component film is directed towards the port.

Precondition samples at about 23° C.±2° C. and about 50%±2% relative humidity for 2 hours prior to testing.

Place the specimen film on the spectrophotometer. The specimen should completely cover the port.

A total of three substantially identical samples are analyzed and their L*, a*, b* results recorded. Calculate and report the average values and standard deviation for the film measurements to the nearest 0.01%. Analysis is done for the film made from the material of the core component and for the film made from the material of the sheath component.

Record the averaged values as L*i, a*i and b*i for the film specimen of core component alone, and the averaged values as L*2, a*2 and b*2 for the specimen with the film of core component covered by the film of the sheath component. Calculate and report the color difference (delta E*) between the core component film taken alone, and the core component film covered with the sheath component film, using the following equation:

$$\text{delta } E^* = \sqrt{(L_2^* - L_1^*)^2 + (a_2^* - a_1^*)^2 + (b_2^* - b_1^*)^2}$$

Opacity Measurement Method

The opacity of a material is the degree to which light is blocked by that material. A higher opacity value indicates a higher degree of light block by the material. Opacity may be measured using a 0.deg. illumination/45.deg. detection, circumferential optical geometry, spectrophotometer with a computer interface such as the HunterLab LabScan® XE running Universal Software (available from Hunter Associates Laboratory Inc., Reston, VA). Instrument calibration and measurements are made using the standard white and black calibration plates provided by the vendor. All testing is performed in a room maintained at about 23° C.±2° C. and about 50%±2% relative humidity. Configure the spectrophotometer for the XYZ color scale, D65 illuminant, 10.deg. standard observer, with UV filter set to nominal. Standardize the instrument according to the manufacturer's procedures using the 1.20 inch port size and 1.00 inch area view. After calibration, set the software to the Y opacity procedure.

To obtain the specimen, the same procedure is followed as set above for measurement of the L*, a*, and b* values. For the opacity measurement, a film layer is only needed for the material of the sheath component. Precondition samples at about 23° C.±2° C. and about 50%±2% relative humidity for 2 hours prior to testing.

Place the specimen film (=the film of the sheath component alone, i.e. without the film of the core component underneath) over the measurement port. The specimen should completely cover the port with the first outer surface directed toward the port. Cover the specimen with the white standard plate. Take a reading, then remove the white tile and replace it with black standard tile without moving the specimen. Obtain a second reading, and calculate the opacity as follows:

$$\text{Opacity} = [Y \text{ value (black backing)} / Y \text{ value (white backing)}] \times 100\%$$

A total of five substantially identical samples of films made from sheath component material are analyzed and their opacity results recorded. Calculate and report the average opacity and standard deviation for the film measurements to the nearest 0.01%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of the present disclosure.

What is claimed is:

1. An absorbent article comprising a topsheet forming at least a portion of a wearer-facing surface of the absorbent article, a backsheet forming at least a portion of a garment-facing surface of the absorbent article, and an absorbent core interposed between the topsheet and the backsheet,
   wherein the absorbent article comprises a nonwoven material,
   wherein the nonwoven material comprises at least 20%, by weight of the nonwoven material, of core/sheath bicomponent fibers,
   wherein the core component of the core/sheath bicomponent fibers is formed of polyethylene terephthalate (PET) and the sheath component is formed of a thermoplastic polymer other than PET,
   wherein the PET does not comprise a phosphorous compound;
   wherein the PET comprises less than 150 ppm of antimony, and
   wherein the core component has an a* value unequal to zero and a b* value unequal to zero.

2. The absorbent article of claim 1, wherein the sheath component has an opacity of at least 10%.

3. The absorbent article of claim 1, wherein a delta E* value between the core component and the core component covered by the sheath component is at least 1.0.

4. The absorbent article of claim 1, wherein the PET comprises less than 100 ppm of antimony.

5. The absorbent article of claim 1, wherein the a* value of the core component is less than −0.6.

6. The absorbent article of claim 1, wherein the b* value of the core component is higher than 1.5.

7. The absorbent article of claim 1, wherein the sheath component has a content of titanium dioxide of from 0.5% to 2.0%, by weight of the sheath component.

8. The absorbent article of claim 1, wherein the sheath component forms at least 25%, by weight of the bicomponent fiber.

9. The absorbent article of claim 1, wherein the core/sheath bicomponent fiber has a concentric core/sheath configuration.

10. The absorbent article of claim 1, wherein the bicomponent fibers have a circular cross-section.

11. The absorbent article of claim 1, wherein the sheath forms at least 30% of a diameter of the bicomponent fiber.

12. The absorbent article of claim 1, wherein the nonwoven material forms the topsheet and/or the backsheet.

13. The absorbent article of claim 1, wherein the nonwoven material is provided between the topsheet and the absorbent core.

14. The absorbent article of claim 1, wherein the absorbent article comprises an acquisition layer which is provided between the absorbent core and the topsheet, and wherein the nonwoven material forms at least a portion of the acquisition layer.

15. The absorbent article of claim 1, wherein the absorbent core comprises a combination of cellulose fibers and superabsorbent polymer particles, wherein the absorbent core comprises areas which are free of cellulose fibers and superabsorbent polymer particles, and wherein the areas are elongated areas having a length of from 20% and 80% by total longitudinal dimension of the absorbent article.

16. The absorbent article of claim 1, wherein the PET is provided as a homopolymer, a copolymer (co-PET), or a combination thereof.

17. The absorbent article of claim 1, wherein the PET does not comprise any of the following: dyes, pigments, hues, and optical brighteners.

18. The absorbent article of claim 1, wherein the nonwoven material comprises poly-lactic acid (PLA).

19. The absorbent article of claim 1, wherein the nonwoven material comprises natural fibers.

20. The absorbent article of claim 19, wherein the natural fibers comprise cotton fibers and/or cellulose fibers.

* * * * *